United States Patent [19]
Jarrett et al.

[11] Patent Number: 6,130,271
[45] Date of Patent: *Oct. 10, 2000

[54] DEFORMABLE ABSORBABLE SURGICAL DEVICE

[75] Inventors: Peter Kendrick Jarrett, Southbury, Conn.; Donald James Casey, Mars, Pa.; Steven L. Peake, Ridgefield, Conn.

[73] Assignee: Tyco Group S.a.r.l., Luxembourg, Luxembourg

[*] Notice: This patent is subject to a terminal disclaimer.

[21] Appl. No.: 09/005,143

[22] Filed: Jan. 9, 1998

Related U.S. Application Data

[63] Continuation of application No. 08/362,997, Dec. 23, 1994, abandoned, which is a continuation-in-part of application No. 07/821,731, Jan. 13, 1992, Pat. No. 5,376,102, which is a continuation-in-part of application No. 07/548,802, Jul. 6, 1990, Pat. No. 5,080,665.

[51] Int. Cl.$^7$ .............................. A61B 17/03; C08G 63/64
[52] U.S. Cl. ........................ 523/113; 525/411; 525/415; 528/361; 606/219; 606/230; 606/231; 606/37
[58] Field of Search ............................ 523/113; 525/411, 525/415; 528/361; 606/230, 231, 219

[56] References Cited

U.S. PATENT DOCUMENTS

| | | | |
|---|---|---|---|
| 4,052,988 | 10/1977 | Doddi et al. | 128/335.5 |
| 4,243,775 | 1/1981 | Rosensaft et al. | 525/415 |
| 4,279,249 | 7/1981 | Vert et al. | 128/98 D |
| 4,300,565 | 11/1981 | Rosensaft et al. | 128/333.5 |
| 4,429,080 | 1/1984 | Casey et al. | 525/415 |
| 4,539,981 | 9/1985 | Tunc | 128/92 B |
| 4,550,449 | 11/1985 | Tunc | 623/16 |
| 4,646,741 | 3/1987 | Smith | 128/334 R |
| 4,655,777 | 4/1987 | Dunn et al. | 623/16 |
| 4,705,820 | 11/1987 | Wang et al. | 524/381 |
| 4,711,241 | 12/1987 | Lehmann | 128/335.5 |
| 4,743,257 | 5/1988 | Törmälä et al. | 623/16 |
| 4,744,365 | 5/1988 | Kaplan et al. | 128/335.5 |
| 4,781,183 | 11/1988 | Casey et al. | 128/99 YP |
| 4,788,979 | 12/1988 | Jarrett et al. | 128/335.5 |
| 4,839,130 | 6/1989 | Kaplan et al. | 264/235 |
| 4,844,854 | 7/1989 | Kaplan et al. | 264/235 |
| 4,891,263 | 1/1990 | Kotliar et al. | 428/225 |
| 4,916,193 | 4/1990 | Tang et al. | 525/413 |
| 4,916,207 | 4/1990 | Boyle, Jr. et al. | 523/114 |
| 4,920,203 | 4/1990 | Tang et al. | 523/115 |
| 4,923,470 | 5/1990 | Dumican | 623/11 |
| 5,080,665 | 1/1992 | Jarrett et al. | 606/219 |
| 5,324,307 | 6/1994 | Jarrett et al. | 606/219 |
| 5,376,102 | 12/1994 | Jarrett et al. | 525/415 |

FOREIGN PATENT DOCUMENTS

| | | | |
|---|---|---|---|
| 0185453 | 6/1986 | European Pat. Off. | 606/219 |
| WO84/03035 | 8/1984 | WIPO . | |
| WO89/05664 | 6/1989 | WIPO . | |

OTHER PUBLICATIONS

Bucknall, C.B., Toughened Plastics, Applied Science Publishers (1977).
L.H. Sperling, Introduction to Physical Polymer Science (1986), p. 17.
Yee, A.F. and Pearson, R.A., "Toughening Mechanisms in Elastomers–Modified Epoxies Part 1 Mechanical Studies", J. Mat. Sci., v.21, 1986, pp. 2462–2474.
Pearson, R.A. and Yee, A.F., "Toughening Mechanisms in Elastomer–Modified Epoxies Part 2 Microscopy Studies", J. Mat. Sci., v.21, 1986, pp. 2475–2488.
A.F. Yee, "Impact Resistant Materials", Encyclopedia of Polymer Science and Engineering, pp. 59–68 (1987).
Whittington's Dictionary of Plastics, p. 250 (1993).
L.A. Utracki, et al. "Multiphase Polymers: Blends and Ionomers", ACS Symposium Series 395, Jun. 5–11, 1988, p. 3.
Comprehensive Polymer Science, vol. 2, section 15.3, pp. 526–532 (1989).
Soderquist, M.E. and Dion, R.P., "High Impact Polystyrene", Encyclopedia of Polymer Science and Engineering, vol. 15, pp. 88–97 (1989).

*Primary Examiner*—Andrew E. C. Merriam
*Attorney, Agent, or Firm*—Fitzpatrick, Cella, Harper & Scinto

[57] ABSTRACT

A deformable surgical repair device is manufactured from a block or graft copolymer. The copolymer comprises a plurality of first linkages selected from the group consisting of glycolic acid ester and lactic acid ester linkages, and mixtures thereof, and a plurality of second linkages selected from the group consisting of 1,3-dioxan-2-one; 1,4-dioxan-2-one and ε-caprolactone linkages. The plurality of first linkages comprises at least about 50 up to about 90 mole percent of the copolymer. In an alternative Claim, the deformable surgical repair device is manufactured from a blend of a first and a second absorbable polymer. The first absorbable polymer comprises a plurality of linkages selected from the group consisting of glycolic acid ester and lactic acid ester linkages, and mixtures thereof. The second absorbable polymer comprises a plurality of linkages selected from the group consisting of 1,3-dioxan-2-one; 1,4-dioxan-2-one and ε-caprolactone linkages. The first absorbable polymer comprises at least about 50 up to about 90 weight percent of the blend. The device is useful in fracture fixation.

7 Claims, No Drawings

DEFORMABLE ABSORBABLE SURGICAL DEVICE

This application is a continuation of application Ser. No. 08/362,997, filed on Dec. 23, 1994, now abandoned, which is a continuation of application Ser. No. 07/821,731, filed on Jan. 13, 1992, now U.S. Pat. No. 5,376,102, which is a continuation of application Ser. No. 08/548,802, filed on Jul. 06, 1990, now U.S. Pat. No. 5,080,665.

BACKGROUND AND SUMMARY OF THE INVENTION

This invention relates to absorbable polymeric materials possessing an enhanced ability for permanent deformation at room temperature through a crazing mechanism. This invention also relates to the use of these materials in medical device applications that require the material to be reshapable. One such application is in absorbable maxillofacial bone fixation plates where complex fracture site surface contours are often encountered. For comparison, see the Masterpiece™ maxillofacial bone plate system (Storz Instrument Co., MO 63122, USA). Another application is in absorbable surgical clips and staples where improved toughness and ductility are desirable.

The following U.S. Pat. Nos. are pertinent to the present inventions described in this application: 4,243,775, 4,279,249, 4,300,565, 4,539,981, 4,550,449, 4,744,365, 4,788,979, 4,839,130, 4,844,854. Also pertinent is the international patent application WO 89/05664. These patents and the application are incorporated herein by reference.

The modification of glassy polymeric materials for improved toughness is well known in the nonabsorbable polymer art. Perhaps the most notable example of a toughened glassy plastic is high impact polystyrene (HIPS). The following review article describes the property improvements of HIPS: Soderquist, M. E. and Dion, R. P., "High Impact Polystyrene," in *Encyclopedia of Polymer Science and Engineering*, Vol 16, pp. 88–97, John Wiley & Sons, New York, 1989. Many other nonabsorbable polymers have been modified for improved toughness or impact resistance. A general review of this field can be found in Yee, A. F., "Impact Resistant Materials," in *Encyclopedia of Polymer Science and Engineering*, Vol. 8, pp. 59–68, John Wiley & Sons, New York, 1989 and in Bucknall, C. B., *Toughened Plastics*, Applied Science Publishers, London, 1977 and in *Comprehensive Polymer Sciences* Vol. 2, section 15.3, pp. 526–532, C. Booth & C. Price, eds., Pergamon Press, New York, 1989. Generally, toughness and impact resistance have been improved by incorporating a discontinuous rubbery phase in the parent polymer matrix. This has been done by physical blending or by preparation of block or graft copolymers. Similar concepts have been applied to thermosets such as epoxy resins (see Yee, A. F. and Pearson, R. A., "Toughening Mechanisms in Elastomer-Modified Epoxies Part 1 Mechanical Studies," J. Mat. Sci., Vol. 21, 1986, pp. 2462–2474 and Pearson, R. A. and Yee, A. F., "Toughening Mechanisms in Elastomer-Modified Epoxies Part 2 Microscopy Studies," J. Mat. Sci., Vol. 21, 1986, pp. 2475–2488. All of the above cited disclosures are incorporated herein by reference. Although increases of ductility in nonabsorbable rubber modified plastics have been reported, the primary purpose of the modification has been to impart impact resistance and toughness. To our knowledge this property modification method has not been put to use in medical devices, either absorbable or nonabsorbable.

The U.S. Pat. Nos. 4,243,775 and 4,300,565 cited above disclose absorbable polymeric compositions which were thought to form a two phase morphology. These patents do not mention any enhancement of deformability in bending due to the presence of a rubbery phase.

Some other patents (U.S. Pat. Nos. 4,744,365, 4,839,130 and 4,844,854) disclose two phase copolymers of lactide and glycolide. These patents do not mention any enhancement of deformability in bending other than reduced brittleness. Also, the copolymers disclosed in the '365, '130 and '854 patents do not contain a rubbery phase; rather, they contain two semicrystalline glassy phases. The utility of these two phase copolymers are described as a surgical clip or staple. The rubber toughened materials of this application may also be useful as a surgical clip or staple.

None of the prior art mentions the usefulness of materials which can be permanently deformed at room temperature through crazing as a medical device. The U.S. Pat. No. 4,279,249 claims bioabsorbable boneplate devices manufactured from a copolymer of at least 90% units derived from lactic acid and reinforcing fibers made of polyglycolic acid or a copolymer thereof. Nowhere in this patent is it disclosed that the material can be permanently deformed by bending at room temperature, although improved resilience and shock resistance are disclosed. Also, this patent claims a "matrix" polymer of at least 90% lactic acid units.

The present invention describes medical devices made from block copolymers. The block copolymer is composed of a lactide or a lactide/glycolide copolymer and a low glass transition temperature or a rubbery polymer such as polytrimethylene carbonate. It is the presence of the rubbery or soft block which imparts the deformability in bending to the surgical repair devices described in this application.

Other bioabsorbable bone fixation devices have been fashioned from high molecular weight poly(1-lactide); see, e.g. U.S. Pat. Nos. 4,539,981 and 4,550,449. This material does not allow reshaping at room temperature and no mention of such a property is made in these patents.

Block copolymers containing trimethylene carbonate and lactide were exemplified in the international patent application WO 89/05664. The materials exemplified were higher compared to the compositions described in this application in rubbery phase content. In the WO application, no mention was made of ductile properties or the usefulness of such a property in medical devices.

Block copolymers containing trimethylene carbonate, caprolactone, and glycolide as well as block copolymers containing caprolactone and glycolide were exemplified for use as suture coatings in U.S. Pat. No. 4,788,979. These materials were also rich in soft phase forming units. No mention was made of ductile properties in this patent.

The following embodiments summarize the invention:

1. An article of manufacture comprising a deformable surgical repair device, the deformable surgical repair device manufactured from a copolymer, the copolymer selected from the group consisting of a block and graft copolymer, the copolymer comprising a plurality of first linkages selected from the group consisting of glycolic acid ester and lactic acid ester linkages, and mixtures thereof, and a plurality of second linkages selected from the group consisting of 1,3-dioxan-2-one; 1,4-dioxan-2-one and ε-caprolactone linkages, the plurality of first linkages comprising at least about 50 up to about 90 mole percent of the copolymer.

2. The article of embodiment 1 wherein the copolymer is a block copolymer.

3. The article of embodiment 2 wherein the plurality of first linkages comprises lactic acid ester linkages.

4. The article of embodiment 2 wherein the plurality of first linkages comprises glycolic acid ester linkages.

5. The article of embodiment 3 or 4 wherein the plurality of second linkages comprises 1,3-dioxan-2-one linkages.

6. An article of manufacture comprising a deformable fracture fixation device, the deformable fracture fixation device manufactured from a copolymer, the copolymer selected from the group consisting of a block and graft copolymer, the copolymer having a plurality of first linkages comprising lactic acid ester linkages and a plurality of second linkages selected from the group consisting of 1,3-dioxan-2-one and 1,4-dioxan-2-one linkages, the plurality of lactic acid ester linkages comprising more than 50 to about 80 weight percent of the copolymer.

7. The article of embodiment 6 wherein the copolymer is a block copolymer.

8. The article of embodiment 7 wherein the plurality of lactic acid ester linkages comprises about 80 weight percent of the copolymer.

9. The article of embodiment 8 wherein the plurality of second linkages comprises 1,3-dioxan-2-one linkages.

10. An article of manufacture comprising a deformable surgical repair device, the deformable surgical repair device manufactured from a blend of a first and a second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50 up to about 90 weight percent of the blend.

11. The article of embodiment 10 wherein the first absorbable polymer is a homopolymer.

12. The article of embodiment 11 wherein the first absorbable homopolymer consists essentially of lactic acid ester linkages.

13. The article of embodiment 10 wherein the first absorbable polymer is a copolymer.

14. The article of embodiment 12 wherein the second absorbable polymer comprises a plurality of linkages selected from the group consisting of 1,3-dioxan-2-one and 1,4-dioxan-2-one linkages.

15. The article of embodiments 1, 2, 3, 10, 11, 12 or 14 wherein the deformable surgical repair device is a fracture fixation device.

16. The article of embodiment 15 wherein the fracture fixation device is a bone plate.

17. The article of embodiments 1, 2, 3, 10, 11, 12 or 14 wherein the deformable surgical repair device is a clip.

18. The article of embodiments 1, 2, 3, 10, 11, 12 or 14 wherein the deformable surgical repair device is a staple.

19. A surgical composite structure for mammalian tissue comprising:
   a) a reinforcing component prepared from a plurality of fibers, plurality of the fibers manufactured from a biocompatible polymer, and
   b) a bioabsorbable component comprising a copolymer the copolymer selected from the group consisting of a block and graft copolymer, the copolymer comprising a plurality of first linkages selected from the group consisting of glycolic acid aster and lactic acid ester linkages, and mixtures thereof, and a plurality of second linkages selected from the group consisting of 1,3-dioxan-2-ons; 1,4-dioxan-2-one and $\epsilon$-caprolactone linkages, the plurality of first linkages comprising at least about 50 up to about 90 mole percent of the copolymer.

20. The structure of embodiment 19 wherein the reinforcing component is manufactured from an absorbable biocompatible polymer.

21. The structure of embodiment 20 wherein the absorbable biocompatible polymer is selected from the group consisting of a homopolymer or copolymer of polyglycolic acid, polylactic acid, polyhydroxy butyrate and blends of the same, and poly(d-lactic acid) blended with poly(1-lactic acid).

22. The structure of embodiment 19 wherein the reinforcing component is manufactured from a nonabsorbable biocompatible polymer.

23. The structure of embodiment 22 wherein the nonabsorbable biocompatible polymer is selected from the group consisting of polyethylene terephthalate, silk, nylon, polypropylene, polyethylene and polyoxymethylene and blends of the same.

24. The structure of embodiment 19, 20, 21, 22 or 23 wherein the bioabsorbable Component comprises a block copolymer.

25. The structure of embodiment 24 wherein the plurality of first linkages in the block copolymer comprises lactic acid ester linkages.

26. The structure of embodiment 24 wherein the plurality of first linkages in the block copolymer comprises glycolic acid ester linkages.

27. The structure of embodiment 25 or 26 wherein the plurality of second linkages in the block copolymer comprises 1,3-dioxan-2-one linkages.

28. A surgical composite structure for mammalian tissue comprising:
   a) a reinforcing component prepared from a plurality of fibers, plurality of the fibers manufactured from biocompatible polymer, and
   b) a bioabsorbable component comprising a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50 up to about 90 weight percent of the blend.

29. The structure of embodiment 19 wherein the reinforcing component is manufactured from an absorbable biocompatible polymer.

30. The structure of embodiment 20 wherein the absorbable biocompatible polymer is selected from the group consisting of a homopolymer or copolymer of polyglycolic acid, polylactic acid, polyhydroxy butyrate and blends of the same, and poly(d-lactic acid) blended with poly(1-lactic acid).

31. The structure of embodiment 19 wherein the reinforcing component is manufactured from a nonabsorbable biocompatible polymer.

32. The structure of embodiment 22 wherein the nonabsorbable biocompatible polymer is selected from the group consisting of polyethylene terephthalate, silk, nylon, polypropylene, polyethylene and polyoxymethylene and blends of the same.

33. The structure of embodiment 28, 29, 30, 31 or 32 wherein the first absorbable polymer in the bioabsorbable component is a homopolymer.

34. The structure of embodiment 33 wherein the first absorbable homopolymer in the bioabsorbable component consists essentially of lactic acid ester linkages.

35. The structure of embodiment 28, 29, 30, 31 or 32 wherein the first absorbable polymer in the bioabsorbable component is a copolymer.

36. The structure of embodiment 24 wherein the second absorbable polymer in the bioabsorbable component comprises a plurality of linkages selected from the group consisting of 1,3-dioxan-2-one and 1,4-dioxan-2-one linkages.

Referring to the embodiments in subparagraphs 5, 6, 9, 10 and 14, above, and generally as described in this specification, some polymers have been described as linkages of one or more monomers. Some of these monomers are described as cyclic esters, e.g. 1,4-dioxan-2-one. It is to be understood that any person skilled in the art implicitly knows how to make and how to use these monomers to form the polymer linkages and that, therefore, the description of these linkages by the use of this monomeric nomenclature is adequate.

Referring to the embodiments in subparagraphs 1, 6, 10 and 15, above, it is to be clearly understood that the surgical repair and fracture fixation devices include, but are not limited to, those embodiments described in subparagraphs 16 to 18, above. Thus, other devices, e.g. a bone pin, bone rod, bone screw, trocar, prosthetic tubular article, and similar or related molded or extruded devices, are within the scope of this invention. For a general disclosure of medical uses, see columns 4 and 5 in U.S. Pat. No. 4,135,622 issued Jan. 23, 1979, which is incorporated herein by reference.

Referring to subparagraphs 19 and 28, above, the plurality of fibers in the reinforcing component can be matted, chopped, woven, knitted, unidirectional or a fiber tow. The plurality of fibers can also be composed of laminated plies wherein each ply consists of continuous, unidirectional fibers, woven fabric or knitted fabric and the direction of fibers between adjacent plies need not be the same.

Referring, generally, to subparagraphs 19 to 36, above, in the fabrication of the composite structure, it is to be understood that the melting point of the bioabsorbable component must be less than the melting point of the reinforcing component. See also, generally, Example 12.

Referring to the embodiments in subparagraphs 20 and 29, above, it is to be understood that other absorbable polymers can be used beside those described in subparagraphs 21 and 30, above, respectively, other absorbable polymers include those described in the "Description of the Invention," below, subparagraphs 1A. 2A., which description is not exclusive.

DESCRIPTION OF THE INVENTION

This invention relates to absorbable polymeric materials possessing an enhanced ability for permanent deformation at room temperature through a crazing mechanism. This invention also relates to the use of these materials in medical device applications that require the material to be reshapable. Applications where these materials may be useful include the following:

1. Absorbable maxillofacial bone fixation plates.
2. Absorbable bone screws or other fastening devices.
3. Absorbable surgical clips and staples.
4. Absorbable bone fixation rods and screws.

Although not specifically exemplified, it is recognized that a number of materials could be envisioned which could possess similar properties to the exemplified copolymers. To have similar properties, it is necessary that the material have a continuous "hard" phase and a "soft" phase. It is preferred that the soft phase be discontinuous, although this is not required. To form separate hard and soft phases, the hard and soft species must not be fully miscible in their final polymeric form. The final polymeric form could be a block or graft copolymer or a blend of homopolymers and/or copolymers. Alternatively, controlled blending methods could be employed with otherwise miscible polymers to minimize phase mixing in the final article. The following is a list of possible alternative materials which are included in this invention:

1. Block copolymers forming "hard" and "soft" phases.
   A. Hard phase forming monomers
      1. 1-Lactide, d-lactide or meso-lactide
      2. dl-Lactide, variable ratios of d to 1
      3. Glycolide
      4. Mixtures of glycolide and lactide
      5. Other monomers or mixtures of monomers that form absorbable polymers with glass transition temperatures above room temperature.
   B. Soft phase forming monomers
      1. Trimathylene carbonate (1,3-dioxan-2-one)
      2. p-Dioxanone (1.4-dioxan-2-one)
      3. $\epsilon$-Caprolactone (2-oxepanone or oxepan-2-one)
      4. Mixtures of 1, 2 or 3, above
      5. Other monomers or mixtures of monomers that form absorbable polymers with glass transition temperatures below room temperature.
2. Blends of "hard" and "soft" absorbable polymers
   A. Hard phase forming polymers
      1 Poly(1-lactide), poly(d-lactide) or poly(meso-lactide)
      2. Copolymers of 1-lactide, d-lactide or meso-lactide
      3. Polyglycolide
      4. Lactide-glycolide copolymers
      5. Other polymers or copolymers with glass transition temperatures above room temperature.
   B. Soft phase forming polymers
      1. Poly(trimethylene carbonate)
      2. Poly(p-dioxanone)
      3. Poly($\epsilon$-caprolactone)
      4. copolymers of 1, 2, or 3, above
      5. Other polymers or copolymers with glass transition temperatures below room temperature.

The selection of a preferred material will depend on the desired physical properties of the final article. The preferred material will also be determined by the desired in vivo degradation and absorption rates. Several variables can be adjusted to obtain the desired properties. Absorption rate is known to be affected by composition and crystallinity. For example a hard phase of poly(l-lactide) would provide a slow degradation rate due to its hydrophobic, crystalline nature, whereas a copolymer of glycolide and dl-lactide in equal amounts would provide a fast degradation rate due to its more hydrophilic, noncrystalline nature. If increased stiffness or strength is required, an absorbable fiber or fabric reinforcement can be added to make a composite structure. Further improvement of the composite properties can be made by manipulating the location of the reinforcement within the composite, for example, if the reinforcement is placed in the center plane of a laminated structure, the composite would be expected to be stiffer in tension (forces applied parallel to the plane) than in flexion (forces applied normal to the plane), allowing reshaping by bending.

The inventions are further described in the following examples:

EXAMPLE 1

L-Lactide-Trimethylene Carbonate Block Copolymer

Polymerization grade 1,3-dioxan-2-one (trimethylene carbonate, hereafter abbreviated TMC) (97.5 g, 0.995 mole), diethylene glycol (hereafter abbreviated DEG) ($4.20 \times 10^{-2}$ g, $4.0 \times 10^{-4}$ mole), and Dabco T-9 catalyst (a stannous 2-ethylhexanoate catalyst formulation sold by Air Products, Inc., hereafter abbreviated T-9) ($1.35 \times 10^{-2}$ g, $3.3 \times 10^{-5}$ moles) were combined in a stirred reactor at 182° C. The temperature was raised to 188° C. and the mixture was stirred for 1½ hours at this temperature. Polymerization grade 1-lactide (52.5 g, 0.364 mole) was added and the temperature was increased to 200° C. After 45 minutes, the polymer was discharged from the reactor and allowed to solidify.

The resulting polymer had an inherent viscosity (hereafter abbreviated IV) of 0.89 dL/g (0.5 g/dL conc. in $CHCl_3$). The convention to be used to define copolymer composition in this and subsequent examples is "mole percent lactide." This refers to the content of units in the copolymer which would be formed by incorporation of a certain mole percent of lactide monomer into the copolymer. The composition of this copolymer was found to be 20.7 mole percent l-lactide by $^1H$ NMR.

The polymer was dissolved in methylene chloride (5 g/dL) and a film of about 0.003 inch thickness was cast. The resulting material was found to be rubbery at room temperature.

EXAMPLE 2

L-Lactide-Trimethylene Carbonate Block Copolymer

Polymerization grade TMC (97.5 g, 0.995 mole), DEG ($4.20 \times 10^{-2}$ g, $4.0 \times 10^{-4}$ mole), and T-9 catalyst ($1.35 \times 10^{-2}$ g, $3.3 \times 10^{-5}$ moles) were combined in a stirred reactor at 180° C. and stirred at 40 RPM for 1 hour and 20 minutes. Polymerization grade 1-lactide (52.5 g, 0.364 mole) was added and the temperature was increased to 200° C. After 1 hour, the polymer was discharged from the reactor and allowed to solidify. The solid polymer was then devolatilized under reduced pressure at 25° C. to remove residual monomer.

The resulting copolymer had an inherent viscosity of 0.64 dL/g (0.5 g/dL conc. in $CHCl_3$). The composition was found to be 25.7 mole percent l-lactide by $^1H$ NMR.

The polymer was dissolved in methylene chloride (5 g/dL) and a film of about 0.003 inch thickness was cast. The resulting material was found to be rubbery at room temperature.

EXAMPLE 3

L-Lactide-Trimethylene Carbonate Block Copolymer

Polymerization grade TMC (64.99 g, 0.637 mole), DEG ($1.83 \times 10^{-2}$ g, $1.73 \times 10^{-4}$ mole), and T-9 catalyst ($8.0 \times 10^{-3}$ g, $2.0 \times 10^{-5}$ moles) were combined in a stirred reactor at 180° C. and stirred at 40 RPM for 35 minutes. Polymerization grade 1-lactide (154.29 g, 1.07 mole) was added and the temperature was increased to 190° C. After 4 hours, the polymer was discharged from the reactor and allowed to solidify.

The resulting copolymer had an inherent viscosity of 1.01 dL/g (0.5 g/dL conc. in $CHCl_3$). The composition was found to be 62.6 mole percent l-lactide by $^1H$ NMR The plaque to be used for test specimen preparation was formed using a heated hydraulic press. At a press temperature of 200° C., about 23 grams of dry polymer granules were pressed in a 4¼ inch by 4¼ inch by ¹⁄₁₆ inch steel frame between Teflon® coated release liner fabric at 500 pounds of pressure for 4 minutes followed by a pressure increase to 5000 pounds for 4 minutes. The hot plagues were cooled between chilled aluminum plates. The plaques were removed from the frame and annealed in the press at 130° C. for 15 minutes at about 250 pounds (14 psi) pressure.

This material was found to undergo ductile deformation through crazing when bent at room temperature.

EXAMPLE 4

L-Lactide-Trimethylene Carbonate Block Copolymer

Polymerization grade TMC (64.99 g, 0.637 mole), DEG ($1.83 \times 10^{-2}$ g, $1.73 \times 10^{-4}$ mole), and T-9 catalyst ($2.06 \times 10^{-2}$ moles) were combined in a stirred reactor at 180° C. and stirred at 40 RPM for 35 minutes. Polymerization grade 1-lactide (154.29g, 1.07 mole) was added and the temperature was increased to 190° C. After 1 hour and 45 minutes, the polymer was discharged from the reactor and allowed to solidify. The polymer was ground cryogenically and dried in vacuum at 105° C. for 18 hours.

The resulting copolymer had an inherent viscosity of 1.44 dL/g (0.5 g/dL conc. in $CHCl_3$). The composition was found to be 60.5 mole percent l-lactide by $^1HNMR$.

A plaque to be used for test specimen preparation was formed according to Example 3.

This material was found to undergo ductile deformation through crazing when bent at room temperature.

EXAMPLE 5

L-lactide-Trimethylene Carbonate Block Copolymer

Polymerization grade TMC (45.94 g, 0.450 mole), DEG ($1.59 \times 10^{-2}$ g, $1.49 \times 10^{-4}$ mole), and T-9 catalyst ($1.81 \times 10^{-2}$ g, $4.48 \times 10^{-5}$ moles) were combined in a stirred reactor at 180° C. and stirred at 40 RPM for 30 minutes. Polymerization grade 1-lactide (151.35 g, 1.07 mole) was added and the temperature was increased to 195° C. After 2 hours, the polymer was discharged from the reactor and allowed to solidify. The solid polymer was ground cryogenically and was then devolatilized under reduced pressure at 105° C. to remove residual monomer.

The resulting copolymer had an inherent viscosity of 1.49 dL/g (0.5 g/dL conc in $CHCl_3$). The composition was found to be 68.3 mole percent l-lactide by $^1H$ NMR A plaque to be used for test specimen preparation was formed according to Example 3.

The material was found to undergo ductile deformation through crazing when bent at room temperature.

EXAMPLE 6

Dl-Lactide-Trimethylene Carbonate Block Copolymer

Polymerization grade THC (33.2 g, 0.325 mole), DEG ($1.72 \times 10^{-2}$ g, $1.62 \times 10^{-4}$ mole), and T-9 catalyst ($7.6 \times 10^{-3}$ g, $1.87 \times 10^{-5}$ moles) were combined in a stirred reactor at 180° C. and stirred at 40 RPM for 35 minutes. Polymerization grade dl-lactide (186.8 g, 1.296 mole) was added and the temperature was increased to 195° C. After 3 hours and 40 minutes the polymer was discharged from the reactor and allowed to solidify. The solid polymer was ground cryogenically and was then devolatilized under reduced pressure at 25° C. for 18 hours to remove residual monomer.

The resulting copolymer had an inherent viscosity of 1.05 dL/g (0.5 V/dL conc. in $CHCl_3$). The composition was found to be 78.6 mole percent dl-lactide by $^1H$ NMR.

A plaque to be used for test specimen preparation was formed according to Example 3.

This material was found to undergo ductile deformation through crazing when bent at room temperature.

EXAMPLE 7

L-Lactide-Trimethylene Carbonate Block Copolymer

Polymerization grade TMC (33.2 g, 0.325 mole), DEG ($1.72\times10^{-2}$ g, $1.62\times10^{-4}$ mole), and T-9 catalyst ($7.6\times10^{-3}$ g, $1.87\times10^{-5}$ moles) were combined in a stirred reactor at 180° C. and stirred at 40 RPM for 35 minutes. Polymerization grade l-lactide (186.8 g, 1.296 mole) was added and the temperature was increased to 195° C. After 3 hours and 40 minutes, the polymer was discharged from the reactor and allowed to solidify. The solid polymer was ground cryogenically and was then devolatilized under reduced pressure at 150° C. for 18 hours to remove residual monomer.

The resulting copolymer had an inherent viscosity of 1.56 dL/g (0.5 g/dL conc. in $CHCl_3$). The composition was found to be 79.1 mole percent l-lactide by $^1H$ NMR.

A plague to be used for test specimen preparation was formed according to Example 3.

This material was found to undergo ductile deformation through crazing when bent at room temperature.

EXAMPLE 8

L-Lactide-Trimethvlene Carbonate Block Copolymer

Polymerization grade THC (16.1 g, 0.158 mole), DEG ($1.67\times10^{-2}$ g, $1.57\times10^{-4}$ mole), and T-9 catalyst ($6.37\times10^{-3}$ g, $1.57\times10^{-5}$ moles) were combined in a stirred reactor at 180° C. and stirred at 40 RPM for 27 minutes. Polymerization grade l-lactide (203.9 g 1.415 mole) was added and the temperature was increased to 195° C. After 6 hours, the polymer was discharged from the reactor and allowed to solidify. The solid polymer was ground cryogenically and was then devolatilized under reduced pressure at 100° C. for 18 hours to remove residual monomer.

The resulting copolymer had an inherent viscosity of 1.41 dL/g (0.5 g/dL conc. in $CHCl_3$). The composition was found to be 89.6 mole percent l-lactide by $^1H$ NMR.

A plaque to be used for test specimen preparation was formed according to Example 3.

This material was found to undergo a small amount of ductile deformation and crazing before breaking when bent at room temperature.

EXAMPLE 9

L-Lactide-Trimethylene Carbonate Block Copolymer

Polymerization grade Tic (7.66 g, 0.075 mole), DEG ($1.69\times10^{-2}$ g, $1.59\times10^{-4}$ mole), and T-9 catalyst ($1.82\times10^{-3}$ g, $4.45\times10^{-5}$ moles) were combined in a stirred reactor at 180° C. and stirred at 40 RPM for 21 minutes. Polymerization grade l-lactide (205.34 g, 1.425 mole) was added and the temperature was increased to 195° C. After 3 hours and 40 minutes, the polymer was discharged from the reactor and allowed to solidify. The solid polymer was ground cryogenically and was then devolatilized under reduced pressure at 100° C. for 18 hours to remove residual monomer.

The resulting copolymer had an inherent viscosity of 1.65 dL/g (0.5 g/dL conc. in $CHCl_3$). The composition was found to be 95.3 mole percent l-lactide by $^1H$ NMR.

A plaque to be used for test specimen preparation was formed according to Example 3.

This material was not found to undergo ductile deformation when bent at room temperature.

EXAMPLE 10

Thermal Analysis of Lactide-THC Copolymers

Samples of copolymers from Examples 3 to 9 were analyzed by differential scanning calorimetry (DSC). Scanning conditions were from −40° C. to 200° C. at 20° C. minimum under nitrogen. Those copolymers which formed two amorphous phases are identified by two glass transition temperatures (Tg(1) and Tg(2)). All samples except Example 5, which was made using dl-lactide, also had a crystalline phase characterized by the melting point (Tm) and the enthalpy of fusion (ΔHf). The results of this analysis are shown in Table 1.

TABLE 1

| Polymer From Example | Mole % 1-Lac | Tg (1) (° C.) | Tg (2) (° C.) | Tm (° C.) | ΔHf (cal/g) |
|---|---|---|---|---|---|
| 3 | 62.5 | −8.8 | 55.8 | 167.6 | 7.28 |
| 4 | 60.5 | −12.5 | 57.8 | 171.4 | 8.76 |
| 5 | 68.3 | −10.3 | 57.3 | 171.1 | 8.86 |
| 6 | 78.8 (dl) | −4.1 | 49.4 | — | — |
| 7 | 79.1 | −12.5 | 59.4 | 172.7 | 11.63 |
| 8 | 89.6 | — | 60.3 | 175.0 | 11.85 |
| 9 | 95.3 | — | 65.8 | 174.8 | 12.12 |

Example 11

Mechanical Testing of Lactide-TMC Copolymers

Plaques made in Examples 4 through 8 were cut into specimens for testing according to ASTM methods D638 (tensile) and D790 (flexural). The results of this testing are included in Table 2. For the tensile tests, five replicates were used, and the mean values are reported in Table 2. The flexural values reported in Table 2 are the means for four replicates.

TABLE 2

| Sample From Example | Mole % 1-lac | At Break | | | At Yield | |
|---|---|---|---|---|---|---|
| | | Modulus ($10^3$ psi) | Strength ($10^3$ psi) | Strain ($10^1$%) | Strength (10 Dsi) | Strain (%) |
| Tensile Results (ASTM D638) | | | | | | |
| 4 | 60.5 | 240 | 4.6 | 10 | 4.9 | 3.9 |
| 5 | 68.3 | 310 | 5.7 | 12 | 6.3 | 3.7 |
| 6 | 78.8 (d1) | 400 | 4.4 | 2.0 | 6.6 | 2.4 |
| 7 | 79.1 | 400 | 6.3 | 0.5 | 7.6 | 2.7 |
| 8 | 89.6 | 480 | 7.3 | 0.43 | 8.7 | 2.4 |
| 9 | 95.3 | 520 | 8.1 | 0.18 | — | — |
| Flexural Results (ASTM D790) | | | | | | |
| 4 | 60.5 | 260 | 7.5 | 12 | 9.0 | 5.5 |
| 5 | 68.3 | 340 | 9.4 | 12 | 11.4 | 5.1 |
| 6 | 78.8 (d1) | 390 | 7.7 | 11 | 10.4 | 3.8 |
| 7 | 79.1 | 480 | 11.8 | 12 | 14.7 | 4.8 |
| 8 | 89.6 | 620 | 17.2 | 6.15 | 18.1 | 4.8 |
| 9 | 95.3 | 710 | 14.5 | 2.16 | — | — |

The flexural and tensile results indicate that the copolymers with 60 to 90 percent lactide form materials which will undergo ductile deformation through crazing. For a bone plate application, it is considered desirable to have the highest modulus and yield strength, while maintaining ductility. The preferred composition for the bone plate application, in the case of lactide-TMC block copolymers, would, therefore, be 80 to 90 percent lactide. Above 90 percent lactide, the sample loses ductility, and below 80 percent lactide, the modulus and yield strength continue to decrease without any advantage in ductility as measured by strain at break in flexure.

EXAMPLE 12

Composite Fabrication

A composite was fabricated in the following manner. Poly(glycolic acid) (PGA) fiber (100 g/denier) was wound around a 7¾' square stainless steel plate. The fiber covered both sides of the plate over a section measuring 3'×7¾' with the long dimension aligned with the fiber. The weight of fiber used for this operation was 12.0 g.

A 10 g/dL solution of the polymer of Example 7 was prepared in methylene chloride. Polymer was then brushed onto the fiber and air dried. This was repeated several times. The material was then consolidated in a heated press at 170° C. and cooled to room temperature. This allowed for the fiber to be cut and the two halves removed from front and back side of the plate. Additional polymer solution was applied to the two sections. This was continued until a total of 19.0 g of polymer was added to the fiber. The two halves were then vacuum pressed to a thickness of 1/16' at a temperature of 170° C. The composite was removed from the press and annealed at 110° C. in an air oven for twenty minutes. The final weight fraction of PGA in the composite was 39%.

The plate was cut into ½"×2½' tensile specimens and tested according to ASTM D638. The tensile modulus was $0.99 \times 10^6$ psi and the tensile strength was $37.0 \times 10^3$ psi.

Two tensile specimens were strained in flexure (ASTM D790) to 5% in an Instron test machine. When the load was relieved, the specimens were permanently deformed to approximately 2% strain. Flexural modulus was $1.27 \times 10^6$ psi and flexural stress at 5% strain was $21.6 \times 10^3$ psi.

We claim:

1. A surgical composite structure for mammalian tissue comprising:
    (a) a reinforcing component prepared from a plurality of fibers, the plurality of fibers manufactured from a biocompatible polymer, and
    (b) a permanently deformable at ambient temperature bioabsorbable component consolidated around said plurality of fibers to form a matrix, the bioabsorbable component having a flexural strain at break of greater than about 25% and a flexural strain at yield of greater than about 3%; the bioabsorbable component comprising (i) a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50up to about 90 weight percent of the blend, or (2) a copolymer selected from the group consisting of a block and graft copolymer, the copolymer comprising a plurality of first linkages selected from the group consisting of glycolic acid ester and lactic acid ester linkages, and mixtures thereof, and a plurality of second linkages selected from the group consisting of 1,3-dioxan-2-one; 1,4-dioxan-2-one and $\epsilon$-caprolactone linkages, the plurality of first linkages comprising at least about 50 up to about 90 mole percent of the copolymer.

2. A surgical composite structure for mammalian tissue comprising:
    a) a reinforcing component prepared from a plurality of fibers, the plurality of fibers manufactured from a bioabsorbable polymer, and
    b) a deformable at ambient temperature bioabsorbable component consolidated around said plurality of fibers to form a matrix, the bioabsorbable component comprising (1) a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50 up to about 90 weight percent of the blend, or (2) a copolymer selected from the group consisting of a block and graft copolymer, the copolymer comprising a plurality of first linkages selected from the group consisting of glycolic acid ester and lactic acid ester linkages, and mixtures thereof, and a plurality of second linkages selected from the group consisting of 1,3-dioxan-2-one; 1,4-dioxan-2-one and $\epsilon$-caprolactone linkages, the plurality of first linkages comprising at least about 50 up to about 90 mole percent of the copolymer.

3. A surgical composite structure for mammalian tissue comprising:
    (a) a reinforcing component prepared from a plurality of fibers, the plurality of fibers manufactured from a biocompatible polymer, and
    (b) a permanently deformable at ambient temperature bioabsorbable component consolidated around said plurality of fibers to form a matrix, the bioabsorbable component having a flexural strain at break of greater than about 25% and a flexural strain at yield of greater than about 3%; the bioabsorbable component comprising (i) a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50 up to about 90 weight percent of the blend.

4. A surgical composite structure for mammalian tissue comprising:
    a) a reinforcing component prepared from a plurality of fibers, the plurality of fibers manufactured from a bioabsorbable polymer, and
    b) a bioabsorbable matrix consolidated around the plurality of fibers, the bioabsorbable matrix comprising a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and $\epsilon$-caprolactone linkages, the first absorbable polymer comprising at least about 50 up to about 90 weight percent of the blend.

5. A surgical composite structure for mammalian tissue comprising:

(a) a reinforcing component prepared from a plurality of fibers, the plurality of fibers manufactured from a bioabsorbable polymer, and (b) a bioabsorbable matrix consolidated around the plurality of fibers, the bioabsorbable matrix comprising (1) a blend of a first and second absorbable polymer, the first absorbable polymer comprising a plurality of linkages selected from the group consisting of glycolic acid ester and lactic acid ester linkages, and mixtures thereof, and the second absorbable polymer comprising a plurality of linkages selected from the group consisting of 1,3-dioxan-2-one; 1,4-dioxan-2-one and ε-caprolactone linkages, the first absorbable polymer comprising at least about 50 up to about 90 weight percent of the blend, or (2) a copolymer selected from the group consisting of a block and graft copolymer, the copolymer comprising a plurality of first linkages selected from the group consisting of glycolic acid ester and lactic acid ester linkages, and mixtures thereof, and a plurality of second linkages selected from the group consisting of 1,3-dioxan-2-one; 1,4-dioxan-2-one and ε-caprolactone linkages, the plurality of first linkages comprising at least about 50 up to about 90 mole percent of the copolymer.

6. An article of manufacture comprising an absorbable surgical fastener manufactured from:

a polymer blend composition containing:
(a) a first absorbable polymer including a plurality of linkages selected from the group consisting of glycolic acid ester linkages, lactic acid ester linkages and mixtures thereof; and
(b) a second absorbable polymer including a plurality of linkages selected from the group consisting of 1,3-dioxan-2-one and e-caprolactone linkages, the first absorbable polymer being present in the blend in an amount from at least about 50 weight percent up to about 99 weight percent based on the total weight of the blend a copolymer selected from the group consisting of a block and graft copolymer, the copolymer comprising:
(a) a plurality of first linkages selected from the group consisting of glycolic acid ester and lactic acid linkages, and mixtures thereof, and
(b) a plurality of second linkages selected from the group consisting of 1,3-dioxan-2-one and ε-caprolactone linkages, the plurality of first linkages comprising at least about 50 up to about 90 mole percent of the copolymer.

7. The surgical composite structure of claim 1 in which the plurality of fibers are manufactured from a bioabsorbable polymer.

* * * * *

UNITED STATES PATENT AND TRADEMARK OFFICE
CERTIFICATE OF CORRECTION

PATENT NO.    : 6,130,271
DATED         : October 10, 2000
INVENTOR(S)   : Peter Kendrick Jarrett, et al.

It is certified that error appears in the above-identified patent and that said Letters Patent is hereby corrected as shown below:

Title page,
[63] Related U.S. Application Data,
"continuation-in-part" should read -- continuation -- (both occurrences).

[73] Assignee,
"Assignee: Tyco Group S.a.r.l., Luxembourg, Luxembourg" should read
-- Assignee: Sherwood Services, AG Schaffhausen, Switzerland --.

Column 3,
line 67, "1,3-dioxan-2-ons;" should read -- 1,3-dioxan-2-one; --;

Column 6,
Line 24, "(1.4-dioxan-2-one)" should read -- 1,3-dioxan-2-one) --;
Line 43, "copolymers" should read -- Copolymers --.

Column 8,
Line 55, "THC" should read -- TMC --.

Column 9,
Line 28, "L-Lactide-Trimethvlene" should read -- L-Lactide-Trimethylene --;
Line 51, "Tic" should read -- TMC --.

Column 10,
Line 5, "Lactide-THC" should read -- Lactide-TMC --;
Table 2, "(10 Dsi)" should read -- (10 psi) --.

Column 11,
Line 10, "7¾" should read -- 7¾" --;
Line 11, "3'x7¾'" should read -- 3"x7¾" --;
Line 23, "1/16'" should read -- 1/16" --;
Line 28, "½" x 2½'" should read -- ½" x 2½" --.
Line 57, "50up" should read -- 50 up --.

UNITED STATES PATENT AND TRADEMARK OFFICE
CERTIFICATE OF CORRECTION

PATENT NO. : 6,130,271
DATED : October 10, 2000
INVENTOR(S) : Peter Kendrick Jarrett, et al.

It is certified that error appears in the above-identified patent and that said Letters Patent is hereby corrected as shown below:

<u>Column 13,</u>
Line 3, "polymer", and (b)" should read -- polymer and (b) --;

<u>Column 14,</u>
Line 12, "blend" should read -- blend. --;
Lines 13-22, should be deleted.

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*